United States Patent [19]

Burns et al.

[11] Patent Number: 4,634,551

[45] Date of Patent: Jan. 6, 1987

[54] BLEACHING COMPOUNDS AND COMPOSITIONS COMPRISING FATTY PEROXYACIDS SALTS THEREOF AND PRECURSORS THEREFOR HAVING AMIDE MOIETIES IN THE FATTY CHAIN

[75] Inventors: Michael E. Burns, West Chester, Ohio; Frederick E. Hardy, Newcastle upon Tyne, England

[73] Assignee: Procter & Gamble Company, Cincinnati, Ohio

[21] Appl. No.: 740,446

[22] Filed: Jun. 3, 1985

[51] Int. Cl.$^4$ .................. C11D 3/395; C11D 7/38; C11D 7/54

[52] U.S. Cl. ......................... 252/102; 8/107; 8/111; 252/98; 252/99; 252/186.38; 252/186.39; 260/404; 260/404.5; 260/507 R; 260/513 N; 260/502 R; 260/546; 548/312; 548/341; 560/42; 560/145; 560/170; 562/439; 562/457; 568/566; 568/568

[58] Field of Search ............. 252/98, 102, 99, 186.38, 252/186.39; 260/507 R, 513 N, 546, 502, 404, 404.5; 568/566, 568; 560/145, 42, 170; 562/439, 457; 8/107, 111; 548/312, 341

[56] References Cited

U.S. PATENT DOCUMENTS

| | | | |
|---|---|---|---|
| 4,221,675 | 9/1980 | Schiermann et al. | 560/250 |
| 4,225,452 | 9/1980 | Leigh | 252/102 |
| 4,225,577 | 9/1980 | Tilly et al. | 424/5 |
| 4,283,301 | 8/1981 | Diehl | 252/102 |
| 4,412,934 | 11/1983 | Chung et al. | 252/186.38 |
| 4,443,623 | 4/1984 | Photis | 560/170 |
| 4,444,674 | 4/1984 | Gray | 252/95 |
| 4,483,781 | 11/1984 | Hartman | 252/174.12 |
| 4,536,314 | 8/1985 | Hardy et al. | 252/102 |

FOREIGN PATENT DOCUMENTS

| | | |
|---|---|---|
| 3304848 | 8/1984 | Fed. Rep. of Germany . |
| 1382594 | 2/1975 | United Kingdom . |

OTHER PUBLICATIONS

USSN 747,468, Hardy et al, filed Jun. 21, 1985.

*Primary Examiner*—Prince E. Willis
*Attorney, Agent, or Firm*—Robert B. Aylor; Richard C. Witte; Thomas H. O'Flaherty

[57] ABSTRACT

This invention relates to bleaching compounds and compositions that provide effective and efficient surface bleaching of textiles over a wide range of bleach solution temperatures. The bleaching compounds of the invention yield a peroxyacid with a polar amide link in the hydrophobic chain when used in the bleaching composition. In a preferred embodiment, the bleaching compositions of the invention are also detergent compositions.

25 Claims, No Drawings

BLEACHING COMPOUNDS AND COMPOSITIONS COMPRISING FATTY PEROXYACIDS SALTS THEREOF AND PRECURSORS THEREFOR HAVING AMIDE MOIETIES IN THE FATTY CHAIN

BACKGROUND OF THE INVENTION

Technical Field

This invention relates to peroxygen bleaching compositions and processes therefor that provide effective bleaching of textiles over a wide range of temperatures.

SUMMARY OF THE INVENTION

The present invention relates to a bleaching compound providing a peroxyacid of the following general formulas:

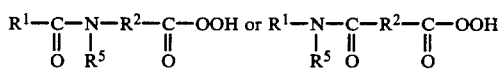

wherein $R^1$ and $R^2$ are alkyl(ene), aryl(ene) or alkaryl(ene) groups containing from about 1 to about 14 carbon atoms and $R^5$ is H or an alkyl, aryl, or alkaryl group containing from about 1 to about 10 carbon atoms.

A group of compounds which provides the above peroxyacids are the magnesium salts of the peroxyacids of the following general formulas:

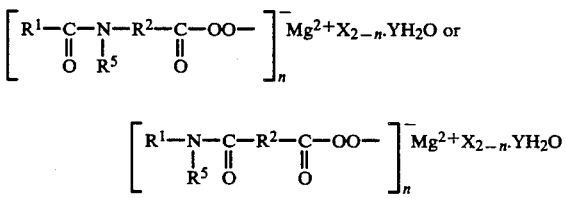

wherein $R^1$, $R^2$ and $R^5$ are as defined for the peroxyacid, X is a compatible anion, n is one or two, and Y is from 0 to about 6.

The peroxyacids may also be formed in situ from a peroxygen bleaching compound capable of yielding hydrogen peroxide in aqueous solution and a bleach activator of the following formulas:

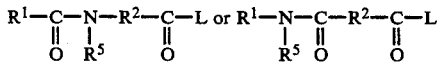

wherein $R^1$, $R^2$ and $R^5$ are as defined for the peroxyacid, and L is a leaving group.

The invention also relates to bleaching compositions which contain one of the above compounds. Where the composition contains the bleach activator, another essential component is a peroxygen bleaching compound capable of yieldng hydrogen peroxide in aqueous solution. In a preferred embodiment, the bleaching compositions are incorporated into detergent compositions.

DETAILED DESCRIPTION OF THE INVENTION

The invention relates to bleaching compounds which provide amide substituted peroxyacids of the following general formula:

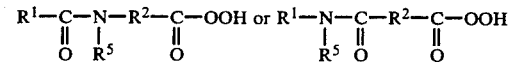

wherein $R^1$ is an aryl or alkaryl group with from about 1 to about 14 carbon atoms, $R^2$ is an alkylene, arylene, and alkarylene group containing from about 1 to about 14 carbon atoms, and $R^5$ is H or an alkyl, aryl, or alkaryl group containing 1 to 10 carbon atoms. $R^1$ preferably contains from about 6 to about 12 carbon atoms. $R^2$ preferably contains from about 4 to about 8 carbon atoms. $R^1$ may be straight chain or branched alkyl, substituted aryl or alkylaryl containing branching, substitution, or both. Analagous structural variations are permissible for $R^2$. The substitution can include alkyl, aryl, halogen, nitrogen, sulfur, and other typical substituent groups of organic compounds. $R^5$ is preferably H or methyl. $R^1$ and $R^5$ should not contain more than 18 carbon atoms total.

The bleaching compounds of the invention provide effective and efficient surface bleaching of textiles which thereby removes stains and/or soils from the textiles. The compounds are particularly efficient at removing dingy soils from textiles. Dingy soils are those that build up on textiles after much usage and washing, and result in a gray or yellow tint on a white textile. These soils are a blend of particulate and greasy materials.

The compounds of the invention provide effective bleaching over a wide range of temperature (5° C. to 85° C.), a preferred range being from about 30° C. to about 60° C.

The presence of the polar amide or substituted amide moiety results in a peroxyacid which has a very low vapor pressure and thus possesses a low odor profile as well as an excellent bleaching performance.

The peroxyacid may be used directly as a bleaching agent. The improved thermal stability of the peroxyacids of the invention, especially when incorporated into the bleaching compositions and detergent compositions described hereinafter is surprising, especially when compared to alkyl peroxyacids, especially the short chain peroxyacids of the prior art, e.g. U.S. Pat. No. 4,412,934, Chung et al, incorporated herein by reference.

While not wishing to be bound by theory it is believed that the polarity of the amide group results in a reduction of vapor pressure of the peroxyacid, and a corresponding increase in melting point.

The substituted amide containing peroxyacids also have a reduced vapor pressure, and show good odor profiles. These compounds are well suited for use in the bleach activator structures provided hereinafter.

THE MAGNESIUM PEROXYCARBOXYLATE

The magnesium salt has the following general formulas:

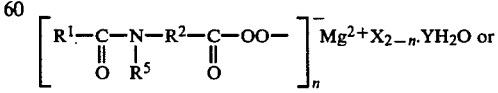

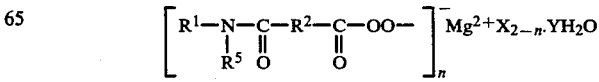

wherein $R^1$, $R^2$ and $R^5$ are as defined for the peroxyacid, X is a compatible anion, n is 1 or 2, and Y is from 0 to about 6.

The compounds are solid and possess good storage under alkaline conditions such as when admixed with a detergent composition. The active oxygen in the magnesium peroxycarboxylate is readily available. This means that the solid magnesium peroxycarboxylates are readily soluble or dispersible and yield solutions containing peroxyacids. When the solution is aqueous, it cannot be distinguished from an aqueous solution prepared from the corresponding peroxyacid and an equivalent amount of magnesium, when the solutions are adjusted to the same pH.

It is believed that the stability of the magnesium salt is due to the fact that the active oxygen atom is nucleophilic rather than electrophilic as it is in the corresponding peroxycarboxylic acid. Nucleophilic agents which would attack an electrophilic oxygen are much more prevalent in bleaching and detergent compositions than electrophilic agents.

The magnesium peroxycarboxylates can be prepared via the process of U.S. Pat. No. 4,483,781, Hartman, issued Nov. 20, 1984, incorporated herein by reference.

THE BLEACH ACTIVATOR

The bleach activators within the invention are amide substituted compounds of the general formulas:

$$R^1-\underset{\underset{O}{\|}}{C}-\underset{\underset{R^5}{|}}{N}-R^2-\underset{\underset{O}{\|}}{C}-L \text{ or } R^1-\underset{\underset{R^5}{|}}{N}-\underset{\underset{O}{\|}}{C}-R^2-\underset{\underset{O}{\|}}{C}-L$$

wherein $R^1$, $R^2$ and $R^5$ are as defined for the peroxyacid, and L can be essentially any suitable leaving group. A leaving group is any group that is displaced from the bleaching activator as a consequence of the nucleophilic attack on the bleach activator by the perhydroxide anion. This, the perhydrolysis reaction, results in the formation of the peroxycarboxylic acid. Generally, for a group to be a suitable leaving group it must exert an electron attracting effect. It should also form a stable entity so that the rate of the back reaction is negligible. This facilitates the neucleophilic attack by the perhydroxide anion.

The L group must be sufficiently reactive for the reaction to occur within the optimum time frame (e.g., a wash cycle). However, if L is too reactive, this activator will be difficult to stabilize for use in a bleaching composition. These characteristics are generally paralleled by the pKa of the conjugate acid of the leaving group, although exceptions to this convention are known. Ordinarily, leaving groups that exhibit such behavior are those in which their conjugate acid has a pKa in the range of from about 4 to about 13, preferably from about 6 to about 11 and most preferably from about 8 to about 11.

Preferred bleach activators are those of the above general formula wherein $R^1$, $R^2$ and $R^5$ are as defined for the peroxyacid and L is selected from the group consisting of:

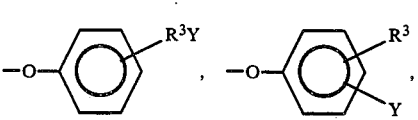

-continued

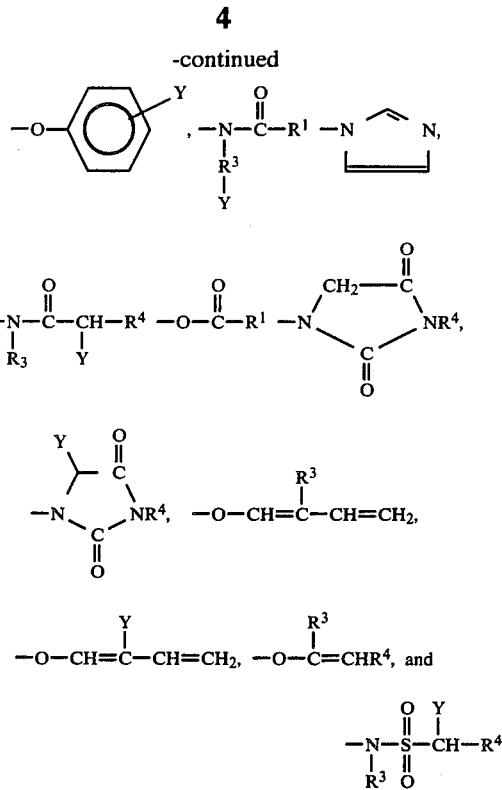

wherein $R^1$ is as defined for the peroxyacid, $R^3$ is an alkyl chain containing from about 1 to about 8 carbon atoms, $R^4$ is H or $R^3$, and Y is H or a solubilizing group. The preferred solubilizing groups are $-SO_3^-M^+$, $-COO^-M^+$, $-SO_4^-M^+$, $(-N^+R_4^3)X^-$ and $O\leftarrow N(R_4^3)$ and most preferably $-SO_3^-M^+$ and $-COO^-M^+$ wherein $R^3$ is an alkyl chain containing from about 1 to about 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion. It should be noted that bleach activators with a leaving group that does not contain a solubilizing group should be well dispersed in the bleaching solution in order to assist in their dissolution.

Preferred bleach activators are those wherein L is a leaving group as previously defined, $R^1$ is an alkyl group containing from about 6 to about 12 carbon atoms, $R^2$ is an alkylene group containing from about 4 carbon atoms to about 8 carbon atoms, and $R^5$ is H or methyl.

Particularly preferred bleach activators are those of the above general formula wherein $R^1$ is an alkyl group and $R^2$ is an alkylene group each containing from about 1 to about 14 carbon atoms, $R^5$ is H, and L is selected from the group consisting of:

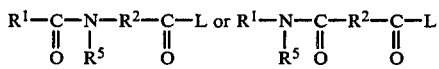

-continued

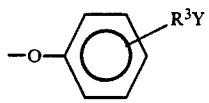

wherein $R^3$ is as defined above and Y is $-SO_3^-M^+$ or $-COO^-M^+$ wherein M is as defined above.

Especially preferred bleach activators are those wherein $R^1$ is a linear alkyl chain containing from about 6 to about 12 carbon atoms, $R^2$ is a linear alkylene chain containing from about 4 to about 8 carbon atoms, $R^5$ is H, and L is selected from the group consisting of:

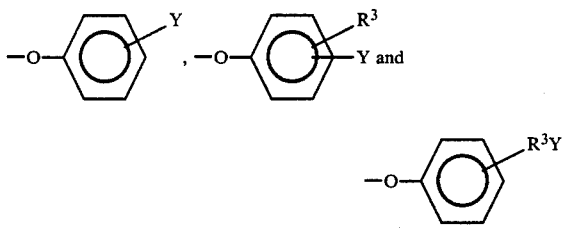

wherein $R^3$ is as defined above and Y is $-SO_3^-M^+$ or $-COO^-M^+$ wherein M is as defined above.

THE BLEACHING COMPOSITIONS

The bleaching compositions of the invention are those which, upon dissolution in aqueous solution, provide a bleaching compound of the formula

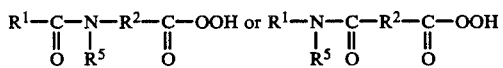

wherein $R^1$, $R^2$ and $R^5$ are as defined for the peroxyacid.

Such compositions provide extremely effective and efficient surface bleaching of textiles which thereby remove stains and/or soils from the textiles. The compositions are particularly effective at removing dingy soils from textiles. Dingy soils are soils that build up on textiles after numerous cycles of usage and washing, and thus, result in a white textile having a gray or yellow tint. These soils tend to be blend of particulate and greasy materials. The removal of this type of soil is sometimes referred to as "dingy fabric clean up".

The bleaching compositions provide such bleaching over a wide range of bleach solution temperatures. Such bleaching is obtained in bleach solutions wherein the solution temperature is at least about 5° C. Inorganic peroxygen bleaches would be ineffective and/or impracticable at temperatures below about 60° C.

This invention also relates to bleaching compositions containing a peroxygen bleach capable of releasing hydrogen peroxide in an aqueous solution and specific bleach activators, hereinafter defined, at specific molar ratios of hydrogen peroxide to bleach activator.

The bleaching mechanism generally, and the surface bleaching mechanism in particular, are not completely understood. However, it is generally believed that the bleach activator undergoes nucleophilic attack by a perhydroxide anion, which is generated from the hydrogen peroxide evolved by the peroxygen bleach, to form a peroxycarboxylic acid. This reaction is commonly referred to as perhydrolysis.

When the activators are used, optimum surface bleaching performance is obtained with bleaching solutions wherein the pH of such solution is between about 8.5 and 10.5 and preferably between 9.5 and 10.5 in order to facilitate the perhydrolysis reaction. Such pH can be obtained with substances commonly known as buffering agents, which are optional components of the bleaching compositions herein.

It is also believed, that the bleach activators within the invention can render peroxygen bleaches more efficient even at bleach solution temperatures wherein bleach activators are not necessary to activate the bleach, i.e., above about 60° C. Therefore, with bleach compositions of the invention, less peroxygen bleach is required to get the same level of surface bleaching performance as is obtained with the peroxygen bleach alone.

The bleaching compositions wherein the bleach activator is used also have, as an essential component a peroxygen bleach capable of releasing hydrogen peroxide in aqueous solution.

THE PEROXYGEN BLEACHING COMPOUND

The peroxygen bleaching compounds useful herein are those cable of yielding hydrogen peroxide in an aqueous solution. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Preferred peroxygen bleaching compounds include sodium perborate, commercially available in the form of mono-, tri- and tetra- hydrate, sodium carbonate peroxyhydrate, sodium pyrophosphate peroxyhydrate, urea peroxyhydrate, and sodium peroxide. Particularly preferred are sodium perborate tetrahydrate and, especially, sodium perborate monohydrate. Sodium perborate monohydrate is especially preferred because it is very stable during storage and yet still dissolves very quickly in the bleaching solution. It is believed that such rapid dissolution results in the formation of higher levels of percarboxylic acid and, thus, enhanced surface bleaching performance.

The level of bleach activator within the compositions of the invention is from about 0.1% to about 60% and preferably from about 0.5% to about 40%. When the bleaching compositions within the invention are also detergent compositions it is preferred that the level of bleach activator is from about 0.5% to about 20%.

OPTIONAL COMPONENTS

As a preferred embodiment, the bleaching compositions of the invention can be detergent compositions. Thus, the bleaching compositions can contain typical detergent composition components such as detergency surfactants and detergency builders. In such preferred embodiments the bleaching compositions are particularly effective. The bleaching compositions of this invention can contain all of the usual components of detergent compositions including the ingredients set forth in U.S. Pat. No. 3,936,537, baskerville et al, incorporated herein by reference. Such components include color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

Enzymes are highly preferred optional ingredients and are incorporated in an amount of from about 0.025% to about 5%, preferably from about 0.05% to about 1.5%. A proteolytic activity of from about 0.01 to about 0.05 Anson units per gram of product is desirable. Other enzymes, including amylolytic enzymes, are also desirably included in the present compositions.

Suitable proteolytic enzymes include the many species known to be adapted for use in detergent compositions. Commercial enzyme preparations such as "Alcalase" solid by Novo Industries, and "Maxatase" sold by Gist-Brocades, Delft, The Netherlands, are suitable. Other preferred enzyme compositions include those commercially available under the tradenames SP-72 ("Esperase") manufactured and sold by Novo Industries, A/S, Copenhagen, Denmark and "AZ-Protease" manufactured and sold by Gist-Brocades, Delft, The Netherlands.

Suitable amylases include "Rapidase" solid by Gist-Brocades and "Termamyl" sold by Novo Industries.

A more complete disclosure of suitable enzymes can be found in U.S. Pat. No. 4,101,457, Place et al, issued July 18, 1978, incorporated herein by reference.

The detergent surfactants can be any one or more surface active agents selected from anionic, nonionic, zwitterionic, amphoteric and cationic classes and compatible mixtures thereof. Detergent surfactants useful herein are listed in U.S. Pat. No. 3,664,961, Norris, issued May 23, 1972, and in U.S. Pat. No. 3,919,678, Laughlin et al, issued Dec. 30, 1975, both incorporated herein by reference. Useful cationic surfactants also include those described in U.S. Pat. No. 4,222,905, Cockrell, issued Sept. 16, 1980, and in U.S. Pat. No. 4,239,659, Murphy, issued Dec. 16, 1980, both incorporated herein by reference. The following are representative examples of detergent surfactants useful in the present compositions.

Water-soluble salts of the higher fatty acids, i.e., "soaps", are useful anionic surfactants in the compositions herein. This includes alkali metal soaps such as the sodium, potassium ammonium, and alkylolammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Useful anionic surfactants also include the water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassiunm alkyl sulfates, especially those obtained by sulfating the higher alcohols ($C_8$–$C_{18}$ carbon atoms) such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11-13}$LAS.

Other anionic surfactants herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Other useful anionic surfactants herein include the water-soluble salts of esters of alpha-sulfonated fatty acids containing from about 6 to 20 carbon atoms in the fatty acid group and from about 1 to 10 carbon atoms in the ester group; water-soluble salts of 2-acyloxyalkane-1-sulfonic acids containing from about 2 to 9 carbon atoms in the acyl group and from about 9 to about 23 carbon atoms in the alkane moiety; water-soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety.

Water-soluble nonionic surfactants are also useful in the compositions of the invention. Such nonionic materials include compounds produced by the condensation of alkylene oxide groups (hydrophilic in nature) with an organic hydrophobic compound, which may be aliphatic or alkyl aromatic in nature. The length of the polyoxyalkylene group which is condensed with any particular hydrophobic group can be readily adjusted to yield a water-soluble compound having the desired degree of balance between hydrophilic and hydrophobic elements.

Suitable nonionic surfactants include the polyethylene oxide condensates of alkyl phenols, e.g., the condensation products of alkyl phenols having an alkyl group containing from about 6 to 15 carbon atoms, in either a straight chain or branched chain configuration, with from about 3 to 12 moles of ethylene oxide per mole of alkyl phenol.

Preferred nonionics are the water-soluble and water-dispersible condensation products of aliphatic alcohols containing from 8 to 22 carbon atoms, in either straight chain or branched configuration, with from 3 to 12 moles of ethylene oxide per mole of alcohol. Particularly preferred are the condensation products of alcohols having an alkyl group containing from about 9 to 15 carbon atoms with from about 4 to 8 moles of ethylene oxide per mole of alcohol.

Semi-polar nonionic surfactants include water-soluble amine oxides containing one alkyl moiety of from about 10 to 18 carbon atoms and two moieties selected from the group of alkyl and hydroxyalkyl moieties of from about 1 to about 3 carbon atoms; water-soluble phosphine oxides containing one alkyl moiety of about 10 to 18 carbon atoms and two moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Ampholytic surfactants include derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic, quaternary, ammonium, phosphonium, and sulfonium compounds in which one of the aliphatic substituents contains from about 8 to 18 carbon atoms.

The level of detergent surfactant that can be employed is from 0% to about 50%, preferably from about 1% to about 30% and most preferably from about 10% to about 25% by weight of the total composition.

In addition to detergent surfactants, detergency builders can be employed in the bleaching compositions. Water-soluble inorganic or organic electrolytes are suitable builders. The builder can also be water-insoluble calcium ion exchange materials; non-limiting examples of suitable water-soluble, inorganic detergent builders include: alkali metal carbonates, borates, phosphates, bicarbonates and silicates. Specific examples of such salts include sodium and potassium tetraborates, bicarbonates, carbonates, orthophosphates, pyrophosphates, tripolyphosphates and metaphosphates.

Examples of suitable organic alkaline detergency builders include: (1) water-soluble amino carboxylates and aminopolyacetates, for example, nitrilotriacetates, glycinates, ethylenediaminetetraacetates, N-(2-hydroxyethyl)nitrilodiacetates and diethylenetriaminepentaacetates; (2) water-soluble salts of phytic acid, for example, sodium and potassium phytates; (3) water-soluble polyphosphonates, including sodium, potassium, and lithium salts of ethane-1-hydroxy-1, 1-diphosphonic acid; sodium, potassium, and lithium salt of ethylene diphosphonic acid; and the like; (4) water-soluble polycarboxylates such as the salts of lactic acid, succinic acid, malonic acid, maleic acid, citric acid, carboxymethyloxysuccinic acid, 2-oxa-1,1,3-propane tricarboxylic acid, 1,1,2,2-ethane tetracarboxylic acid, mellitic acid and pyromellitic acid; and (5) water-soluble polyacetals as disclosed in U.S. Pat. Nos. 4,144,226 and 4,246,495 incorporated herein by reference.

Another type of detergency builder material useful in the present compositions comprises a water-soluble material capable of forming a water-soluble reaction product with water hardness cations preferably in combination with a crystallization seed which is capable of providing growth sites for said reaction product. Such "seeded builder" compositions are fully disclosed in British Patent Specification No. 1,424,406.

A further class of detergency builder materials useful in the present invention are insoluble sodium aluminosilicates, particularly those described in Belgian Pat. No. 814,874, issued Nov. 12, 1974, incorporated herein by reference. This patent discloses and claims detergent compositions containing sodium aluminosilicates having the formula:

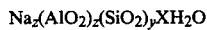

wherein z and y are integers equal to at least 6, the molar ratio of z to y is in the range of from 1.0:1 to about 0.5:1, and X is an integer from about 15 to about 264, said aluminosilicates having a calcium ion exchange capacity of at least 200 milligrams equivalent/gram and a calcium ion exchange rate of at least about 2 grains/gallon/minute/gram. A preferred material is Zeolite A which is:

The level of detergency builder of the bleaching compositions is from 0% to about 70%, preferably from about 10% to about 60% and most preferably from about 20% to about 60%.

Buffering agents can be utilized to maintain the desired alkaline pH of the bleaching solutions. Buffering agents include, but are not limited to many of the detergency builder compounds disclosed hereinbefore. Buffering agents suitable for use herein are those well known in the detergency art.

Preferred optional ingredients include suds modifiers particularly those of suds suppressing types, exemplified by silicones, and silica-silicone mixtures.

U.S. Pat. Nos. 3,933,672, issued Jan. 20, 1976 to Bartolotta et al, and 4,136,045, issued Jan. 23, 1979 to Gault et al, incorporated herein by reference, disclose silicone suds controlling agents. The silicone material can be represented by alkylated polysiloxane materials such as silica aerogels and xerogels and hydrophobic silicas of various types. The silicone material can be described as siloxane having the formula:

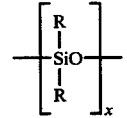

wherein x is from about 20 to about 2,000 and each R is an alkyl or aryl group, especially methyl, ethyl, propyl, butyl and phenyl groups. The polydimethylsiloxanes (both Rs are methyl) having a molecular weight within the range of from about 200 to about 2,000,000, and higher, are all useful as suds controlling agents. Additional suitable silicone materials wherein the side chain groups R are alkyl, aryl, or mixed alkyl or aryl hydrocarbyl groups exhibit useful suds controlling properties. Examples of the like ingredients include diethyl-, dipropyl-, dibutyl-, methyl-, ethyl-, phenylmethylpoly-siloxanes and the like. Additional useful silicone suds controlling agents can be represented by a mixture of an alkylated siloxane, as referred to hereinbefore, and solid silica. Such mixtures are prepared by affixing the silicone to the surface of the solid silica. A preferred silicone suds controlling agent is represented by a hydrophobic silanated (most preferably trimethylsilanated) silica having a particle size in the range from about 10 millimicrons to 20 millimicrons and a specific surface area above about 50 m²/gm. intimately admixed with dimethyl silicone fluid having a molecular weight in the range from about 500 to about 200,000 at a weight ratio of silicone to silanated silica of from about 19:1 to about 1:2. The silicone suds suppressing agent is advantageously releasably incorporated in a water-soluble or water-dispersible, substantially non-surface-active detergent-impermeable carrier.

Particularly useful suds suppressors are the self-emulsifying silicone suds suppressors, described in U.S. Pat. No. 4,073,118, Gault et al, issued Feb. 21, 1978, incorporated herein by reference. An example of such a compound is DB-544, commercially available from Dow Corning, which is a siloxane/glycol copolymer.

Suds modifiers as described above are used at levels of up to approximately 2%, preferably from about 0.1 to about 1½% by weight of the surfactant.

Microcrystalline waxes having a melting point in the range from 35° C.–115° C. and a saponification value of less than 100 represent additional examples of preferred suds control components for use in the subject compositions, and are described in detail in U.S. Pat. No. 4,056,481, Tate, issued Nov. 1, 1977, incorporated herein by reference. The microcrystalline waxes are substantially water-insoluble, but are water-dispersible in the presence of organic surfactants. Preferred microcrystalline waxes have a melting point from about 65° C. to 100° C., a molecular weight in the range from 400–1,000; and a penetration value of at least 6, measured at 77° F. by ASTM-D1321. Suitable examples of the above waxes include: microcrystalline and oxidized microcrystalline petroleum waxes; Fischer-Tropsch and oxidized Fischer-Tropsch waxes; ozokerite; ceresin; montan wax; beeswax; candelilla; and carnauba wax.

Alkyl phosphate esters represent an additional preferred suds control agent for use herein. These preferred phosphate esters are predominantly monostearyl phosphate which, in addition thereto, can contain di- and tristearyl phosphates and monooleyl phosphate, which can contain di- and trioleyl phosphate.

Other suds control agents useful in the practice of the invention are the soap or the soap and nonionic mixtures as disclosed in U.S. Pat. Nos. 2,954,347 and 2,954,348, incorporated herein by reference.

This invention also relates to the process of bleaching textiles with a compound which, when in aqueous solution, yields a peroxyacid of the following formulas:

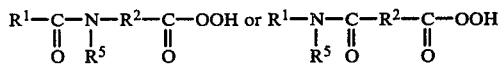

wherein $R^1$ and $R^2$ are alkyl aryl or alkaryl groups with from about 1 to about 14 carbon atoms, and $R^5$ is H or an alkyl, aryl or alkaryl group containing from about 1 to about 10 carbon atoms.

The following examples are given to illustrate the parameters of and compositions within the invention. All percentages, parts and ratios are by weight unless otherwise indicated.

EXAMPLE I

Preparation of N-Lauroyl-6-Aminoperoxycaproic Acid
N-Lauroyl-6-Aminocaproic Acid A one L beaker was charged with 250 mL of 1N sodium hydroxide solution (0.25 mol) and 32.8 g (0.25 mol) of 6-aminocaproic acid. The resulting solution was cooled in an ice bath and, with stirring, a solution of lauroyl chloride (54.7 g, 0.25 mol) in 100 mL ether was added dropwise while maintaining the pH of the stirred solution between 10 and 12 by addition of 10% sodium hydroxide solution. Addition of the lauroyl chloride required 45 min. During this period the reaction mixture became thick with solid and additional volumes of water and ether were added in order to keep the mixture stirrable. Following completion of the lauroyl chloride addition, the ice bath was removed and the mixture was stirred for 1.5 hr. at room temperature. The mixture was then adjusted to pH 2 with concentrated HCl, and the precipitate which formed was removed by filtration and washed with water. The resulting solid was slurried with hexane (200 ml), filtered, and washed 5 times with 100 ml portions of hexane. This hexane slurry/wash procedure was repeated a second time. The resulting solid was air dried to yield 70.7 g (90%) of N-lauroyl-6-aminocaproic acid, mp 87°–90° C. [lit mp 85°–86° C.—E. Jungerman, J. F. Gerecht, and I. J. Krems, J. Amer. Chem. Soc., 78, 172 (1956).]

N-Lauroyl-6-Aminoperoxycaproic Acid

A 250 mL beaker was charged with 35.0 g (0.112 mol) of N-lauroyl-6-aminocaproic acid and 70 mL of 98% methanesulfonic acid. The resulting solution was cooled in an ice bath and, with stirring, 21.2 g of 90% hydrogen peroxide (19.0 g, 0.559 mol of hydrogen peroxide) was added dropwise at a rate so that the temperature of the reaction mixture did not rise above 20° C. (required 15 min.). The resulting solution was stirred at room temperature for 3 hrs., cooled to −15° C., and poured over ice. Ethyl acetate (150 mL) was added, the mixture was warmed to 60° C. in a water bath, and the water layer separated. An additional 100 mL of water was added, the solution again warmed to 60° C. and the water layer separated and discarded. The ethyl acetate solution was cooled to −15° C., and the crystals which formed were removed by filtration and washed with 2×50 mL portions of −15° C. ethyl acetate. The yield of N-lauroyl-6-aminoperoxycaproic acid was 33.1 g; analysis for available oxygen (AvO) indicated 4.31% (theoretical yield=36.9 g having an AvO of 4.86%), mp 70°–75° C.

EXAMPLE II

Preparation of N-Decanoyl-6-Aminoperoxycaproic Acid

N-Decanoyl-6-Aminocaproic Acid

N-decanoyl-6-aminocaproic acid was prepared by reaction of decanoyl chloride with 6-aminocaproic acid according to the procedure described in Example I. From 95.4 g (0.500 mol) of decanoyl chloride and 65.6 g (0.500 mol) of 6-aminocaproic acid was obtained 140 g (98%) of N-decanoyl-6-aminocaproic acid, mp 73°–78° C.

N-Decanoyl-6-Aminoperoxycaproic Acid

A 400 mL beaker was charged with 100 mL of 98% methanesulfonic acid and 500 g (0.175 mol) of N-decanoyl-6-aminocaproic acid. The resulting solution was cooled in an ice bath and, with stirring, 33.1 g of 90% hydrogen peroxide (29.8 g, 0.877 mol of hydrogen peroxide) was added dropwise at a rate such that the temperature of the reaction mixture did not rise above 20° C. The addition required a total of 10 min. The resulting mixture was stirred at room temperature for 3 hrs., cooled to −15° C., and poured into 500 mL of ice water. The precipitated solid was extracted into 200 mL methylene chloride. The methylene chloride solution was separated, washed with 100 mL portions of water until the wash water was neutral (6 washings required), dried over sodium sulfate, and evaporated on a rotary evaporator to yield 51.6 g of white solid having a peroxyacid AvO of 4.93% (theoretical yield=52.7 g of AvO 5.32%).

The N-decanoyl-6-aminoperoxycaproic acid was further purified by recrystallization from 200 mL of ethyl acetate (dissolved in ethyl acetate at 60° C., then cooled to −15° C.) to yield 47.2 g having a peroxyacid AvO of 5.12%, and a mp of 63°–67° C.

EXAMPLE III

Preparation of N-Nonanoyl-6-Aminoperoxycaproic Acid

N-Nonanoyl-6-Aminocaproic Acid

N-nonanoyl-6-aminocaproic acid was prepared by reaction of nonanoyl chloride with 6-aminocaproic acid according to the procedure described in Example I. From 67.3 g (0.381 mol) of nonanoyl chloride and 50.0 g (0.381 mol) of 6-aminocaproic acid was obtained 103 g of N-nonanoyl-6-aminocaproic acid, mp 71°–74° C.

N-Nonaoyl-6-Aminoperoxycaproic Acid

N-nonanoyl-6-aminoperoxycaproic acid was prepared by reaction of N-nonanoyl-6-aminocaproic acid with hydrogen peroxide in 98% methanesulfonic acid according to the procedure described in Example II. From 103 g (0.381 mol) of N-nonanoyl-6-aminocaproic acid, 44 g (1.29 mol) of hydrogen peroxide, and 170 mL of methanesulfonic acid was obtained 74.2 g of N-nonanoyl-6-aminoperoxycaproic acid having a peroxyacid AvO of 5.31% and a mp of 60° C. (theoretical yield=109.5 g of 5.57% AvO).

EXAMPLE IV

Preparation of N-Lauroylaminoperoxyacetic Acid

N-Lauroylglycine

N-Lauroylglycine was prepared by reaction of lauroyl chloride with glycine according to the procedure described in Example I. From 109.4 g (0.500 mol) of lauroyl chloride and 37.6 g (0.500 mol) of glycine was obtained 120.5 g (94%) of N-lauroylglycine, mp 110°–118° C., lit mp 118°–119° C. [E. Jungerman, J. F. Gerecht, and I. J. Krems, *J. Amer. Chem. Soc.* 78, 172 (1956)].

N-Lauroylaminoperoxyacetic Acid

N-Lauroylaminoperoxyacetic acid was prepared by reaction of N-lauroylglycine with hydrogen peroxide in methanesulfonic acid according to the procedure described in Example II. From 50.0 g (0.195 mol) of N-lauroylglycine and 33.1 g (0.973 mol) of hydrogen peroxide in 100 mL methanesulfonic acid was obtained 38.0 g of N-lauroylaminoperoxyacetic acid having an AvO of 3.03% (theoretical yield=53.2 g having an AvO of 5.86%).

EXAMPLE V

Preparation of N-Decanoylaminoperoxyacetic Acid

N-Decanoylglycine

N-Decanoylglycine was prepared by reaction of decanoyl chloride with glycine according to the procedure described in Example I. From 47.7 g (0.25 mol) of decanoyl chloride and 18.8 g (0.25 mol) of glycine was obtained 54.1 g (94%) of N-decanoylglycine, mp 104°–108° C.

N-Decanoylaminoperoxyacetic Acid

N-Decanoylaminoperoxyacetic acid was prepared by reaction of N-decanoylglycine with hydrogen peroxide in methanesulfonic acid according to the procedure described in Example II. From 22.9 g (0.100 mol) of N-decanoylglycine and 17.0 g (0.500 mol) of hydrogen peroxide in 50 mL methanesulfonic acid was obtained 22.4 g of peroxyacid having an AvO of 6.06% (theoretical yield=24.5 g having an AvO of 6.53%), mp 75°–80° C. (melts with gas evolution).

EXAMPLE VI

Preparation of N-Decanoyl-4-Aminophenylperoxyacetic Acid

N-Decanoyl-4-Aminophenylacetic Acid

N-Decanoyl-4-aminophenylacetic acid was prepared by reaction of decanoyl chloride with 4-aminophenylacetic acid according to the procedure described in Example I. From 63.1 g (0.331 mol) of decanoyl chloride and 50.0 g (0.331 mol) of 4-aminophenylacetic acid was obtained N-decanoyl-4-aminophenylacetic acid, mp 156°–159° C.

N-Decanoyl-4-Aminophenylperoxyacetic Acid

N-Decanoyl-4-aminophenylperoxyacetic acid was prepared from N-decanoyl-4-aminophenylacetic acid and hydrogen peroxide in methanesulfonic acid according to the procedure described in Example II. From 70.0 g (0.229 mol) of N-decanoyl-4-aminophenylacetic acid and 39.0 g (1.15 mol) of hydrogen peroxide in 150 mL 98% methanesulfonic acid was obtained 64.9 g of N-decanoyl-4-aminophenylperoxyacetic acid having an AvO of 4.94% (theoretical yield=73.6 g gaving an AvO of 4.99%), mp 121° C.

EXAMPLE VII

Preparation of 6-Decylamino-6-Oxoperoxycaproic Acid

5-Carbomethoxyvaleryl Chloride

This ester/acid chloride was prepared as described in *Org. Synthesis Coll. Vol.* 4, 556 (1963), incorporated herein by reference.

Adipic acid, monomethylester (50.0 g, 0.312 mol) and thionyl chloride (74.3 g, 0.624 mol) were added to a 125 mL Erlenmeyer flask. The flask was fitted with a drying tube and the mixture was allowed to stand at room temperature overnight in a hood. Heptane (100 mL) was added and the excess thionyl chloride was removed on a rotary evaporator. An additional 50 mL of heptane was added and the resulting mixture again evaporated on a rotary evaporator to yield 56.4 g of 5-carbomethoxyvaleryl chloride as a yellow oil.

6-Decylamino-6-Oxocaproic Acid, Methyl Ester

A one L beaker fitted with a mechanical stirrer, ice bath, and pH electrode, was charged with 350 mL of water and 49.1 g (0.312 mol) of decylamine in 100 mL ether. To this stirred mixture was added dropwise a solution of the above 5-carbomethoxyvaleryl chloride in 100 mL ether, concurrent with dropwise addition of 20% sodium hydroxide solution so that the pH of the aqueous layer remained between 10 and 12. Total addition time was 30 min. Following addition of the acid chloride and base, the precipitated solid was removed by filtration and washed with 300 mL hexane. The solid was then stirred with 200 mL hexane, filtered, and washed with 100 mL portions of hexane. After air drying the weight of 6-decylamino-6-oxocaproic acid, methyl ester, was 56.8 g, mp 56°–59° C.

An additional 19.1 g of 6-decylamino-6-oxocaproic acid, methyl ester, was obtained from the filtrate by filtering and washing the collected solid with hexane.

6-Decylamino-6-Oxoperoxycaproic Acid

6-Decylamino-6-oxoperoxycaproic acid was prepared according to the procedure described in Example I for N-decanoyl-6-aminoperoxycaproic acid. Thus, the methyl ester of 6-decylamino-6-oxocaproic acid (29.9 g, 0.10 mol), hydrogen peroxide (17.0 g, 0.50 mol), and 98% methanesulfonic acid (60 mL) were reacted at room temperature for 2 hrs., the reaction mixture poured over ice, and the peroxyacid extracted into 125 mL of 60° C. ethyl acetate. The aqueous layer was discarded and the warm ethyl acetate solution was washed with two 100 mL portions of water. The ethyl acetate solution was transferred to a 250 mL Erlenmeyer flask (rinsed with 25 mL ethyl acetate), reheated to 60° C., and then cooled to −15° C. The crystals of N-decylamino-6-oxoperoxycaproic acid were collected by filtration, washed twice with 50 mL of ice-cold ethyl acetate and air dried. Yield was 21.6 g having peroxyacid AvO of 4.49% (theoretical Yield=30.1 g of 5.32% AvO), and mp 77°-85° C.

EXAMPLE VIII

Preparation of 6-Nonylamino-6-Oxoperoxycaproic Acid

5-Carbomethoxyvaleryl Chloride

5-Carbomethoxyvaleryl chloride was prepared as described in Example VII. From 100 g (0.624 mol) of the monomethylester of adipic acid and 148.6 g (1.248 mol) of thonyl chloride was obtained 111.5 g (0.624 mol) of the ester/acid chloride as a yellow oil.

6-Nonylamino-6-Oxocaproic Acid, Methyl Ester

The ester/acid chloride obtained above was reacted with nonylamine using the procedure described in Example VII for the preparation of 6-decylamino-6-oxocaproic acid, methyl ester. From 111.5 g (0.624 mol of 5-carbomethoxyvaleryl chloride and 89.4 g (0.624 mol) of nonylamine was obtained the methylester of 6-nonylamino-6-oxocaproic acid.

6-Nonylamino-6-Oxoperoxycaproic Acid

6-Nonylamino-6-oxoperoxycaproic acid was prepared according to the procedure described in Example VII for the decylamino derivative. From 100 g (0.350 mol) of the monomethylester of 6-nonylamino-6-oxocaproic acid, 59.6 g (1.75 mol) of hydrogen peroxide, and 300 mL of 98% methanesulfonic acid was obtained 84.7 g of 6-nonylamino-6-oxoperoxycaproic acid of AvO (theoretical=100.7 g and 5.57% AvO), and having mp 83°-87° C.

EXAMPLE IX

Preparation of 6-Benzoylaminoperoxycaproic Acid by Perhydrolysis of Phenolsulfonate Ester of 6-Benzoylaminocaproic Acid 6-Benzoylaminocaproic Acid A 500 mL three-neck flask was fitted with mechanical stirrer, reflux condenser, and nitrogen inlet tube. The flask was flushed with nitrogen and charged with 35.3 g (0.15 mol) of 6-benzoylaminocaproic acid [*Org. Synthesis Coll. Vol.* 2, 76 (1943), incorporated herein by reference] and 150 mL toluene. To the resulting stirred suspension was added 23.3 mL (34.7 g, 0.165 mol) of trifluoroacetic anhydride (Fisher) via a syringe. The suspended solid rapidly dissolved. To this solution was added 29.4 g (0.15 mol) of anhydrous sodium p-phenolsulfonate. The resulting suspension was heated at reflux for 2.5 hrs., cooled in an ice bath, and the precipitated solid was filtered and washed well with ether. After air drying the solid was slurried with 125 mL ethanol, filtered, and washed with ethanol. The resulting white paste was dried under vacuum to give 43.7 g of a hard, white solid. This solid was ground and passed thru 24 mesh screen. Analysis of the nmr spectrum (methyl sulfoxide-$d_6$ solvent) of this solid indicated that it contained 69% of the sodium salt of the phenolsulfonate ester of 6-benzoylaminocaproic acid and 31% sodium p-phenolsulfonate.

6-Benzoylaminoperoxycaproic Acid

Perhydrolysis of the above phenolsulfonate ester to yield 6-benzoylaminoperoxycaproic acid was accomplished according to the following procedure. To 4 L of 95° F. city water was added 5.00 g (1250 ppm) of an alkaline detergent granule, 0.36 g (90 ppm) of sodium perborate monohydrate and 0.46 g (115 ppm) of the sodium salt of the phenolsulfonate ester of 6-benzoylaminocaproic acid (0.67 g of the 69% mixture described above). Perhydrolysis of the ester to form 6-benzoylamino-peroxycaproic acid was followed by analysis of the solution for available oxygen (AvO) using a conventional iodometric titration. Complete conversion of the ester to the peroxyacid would result in the formation of 4.5 ppm AvO. The results obtained for AvO versus time are tabulated below.

| Time (min.) | AvO (ppm) | % of theoretical AvO |
|---|---|---|
| 2 | 3.0 | 67 |
| 7 | 3.2 | 71 |
| 12 | 3.3 | 73 |
| 20 | 3.0 | 67 |

EXAMPLE X

Preparation of the Magnesium Salt of N-Decanoyl-6-Aminoperoxycaproic Acid

A suspension of 2.92 g (0.050 mol) of magnesium hydroxide was prepared by adding 100 mL of 1N sodium hydroxide (0.10 mol) to a solution of 6.02 g (0.050 mol) of magnesium sulfate in 25 mL water. The resulting suspension was added over a 1 min. period to a warm, stirred solution of 30.1 g (0.10 mol) of N-decanoyl-6-aminoperoxycaproic acid in 150 mL ethyl acetate. A heavy precipitate formed immediately. The mixture was stirred for 3 min., filtered, and the collected solid washed with water and ethyl acetate. The weight of magnesium bis-(N-decanoyl-6-aminoperoxycaproate) was 31.7 g, with an available oxygen (AvO) of 3.94%.

EXAMPLE XI

Stability of N-Decanoyl-6-Aminoperoxycaproic Acid

The stability of N-decanoyl-6-aminoperoxycaproic acid was determined, both alone and admixed with an alkaline detergent granule, at a variety of temperatures and humidities. The samples were stored in glass jars having vented tops. The activity of the remaining peroxyacid was determined by conventional iodometric titration for available oxygen. Samples which were admixes of peroxyacid and alkaline detergent granules consisted of 7% peroxyacid and 93% detergent granule. The results of this testing are tabulated below.

| Stability of N—Decanoyl-6-Aminoperoxycaproic Acid % of Original Activity (Stored Alone) | | | | | |
|---|---|---|---|---|---|
| Storage Time (Weeks) | 80° F. | 100° F. | 120° F. | 80° F./15% R.H. | 80° F./60% R.H. |
| 1 | 99 | 98 | 93 | 95 | 98 |
| 2 | 100 | 101 | 98 | 100 | 101 |
| 4 | 100 | 99 | 89 | 100 | 96 |
| 8 | 99 | 93 | 59 | 94 | 101 |
| 14 | 97 | 86 | 7 | 76 | 99 |

| % of Original Activity (Stored with Alkaline Detergent Granule) | | | | | |
|---|---|---|---|---|---|
| Storage Time (Weeks) | 80° F. | 100° F. | 120° F. | 80° F./15% R.H. | 80° F./60% R.H. |
| 1 | 96 | 98 | 90 | 96 | 93 |
| 2 | 89 | 84 | 86 | 89 | 85 |
| 4 | 96 | 89 | 87 | 90 | 85 |
| 8 | 101 | 88 | 66 | 86 | 81 |
| 14 | 96 | 72 | 61 | 59 | 80 |

EXAMPLE XII

Bleaching Performance of N-Decanoyl-6-Aminoperoxycaproic Acid

The bleaching performance of N-decanoyl-6-aminoperoxycaproic acid was determined in a series of experiments which compared the fabric whitening and stain removal of a treatment containing an alkaline detergent granule plus the peroxy acid, with a treatment containing the detergent granule alone.

Thus, to each of two top-loading automatic washing machines was added 5 lbs. of naturally soiled ballast fabrics and 68 liters of 95° F. city water having a hardness of 6 gr/gal. To one machine was added 89 g of an alkaline detergent granule and sufficient N-decanoyl-6-aminoperoxycaproic acid to result in an available oxygen (AvO) level of 3.5 ppm in the wash solution. To the second machine was added only 89 g of the alkaline detergent granule.

To each of the above wash solutions were added two sets of naturally soiled white fabrics and two sets of artificially stained swatches. The washing machines were then allowed to complete their normal washing and rinsing cycles, and the ballast and test fabrics were dryer dried. This procedure was repeated three times, using different sets of ballast fabrics, naturally soiled white fabrics and artificially stained swatches for each replicate.

After completion of the three replicates, the fabrics and swatches were arranged under suitable lighting for comparison of soil and stain removal. Three expert graders compared the extent of removal of the soils and stains using the following scale:
0: no difference between two swatches
1: thought to be a difference
2: certain of a difference
3: certain of a large difference
4: certain of a very large difference In this grinding the naturally soiled white fabrics were compared for improvement in whiteness, and the artificially stained swatches were compared for removal of the stain. The grades obtained were then averaged and normalized to yield the results shown below.

| Treatment and Average Relative Grade | | |
|---|---|---|
| | Detergent Granule Alone | Detergent Granule + 3.5 ppm AvO From N—Decanoyl-6-Aminoperoxycaproic Acid |
| Naturally Soiled Fabrics | | |
| T-shirts | 0 | 2.4 s |
| Dish towels | 0 | 1.1 s |
| Pillowcases | 0 | 2.2 s |
| Artificially Stained Fabrics | | |
| Clay | 0 | 0.4 |
| Spaghetti sauce | 0 | 0.1 |
| Barbecue sauce | 0 | −0.4 |
| Tea | 0 | 3.3 s |
| Grass | 0 | 3.0 s |
| Menstrual blood | 0 | 0.4 |
| Blueberries | 0 | 1.7 s | s = statistically significant difference (confidence level of 90%) relative to the detergent granule alone treatment

EXAMPLE XIII

Bleaching Performance of Magnesium Bis(N-Decanoyl-6-Aminoperoxycaproate)

The bleaching performance of the magnesium salt of N-decanoyl-6-aminoperoxycaproic acid was determined using the procedure described in Example XII. The magnesium salt was added to the wash solution as a finely divided powder suspended in 50 mL methanol. The amount of magnesium salt added was that which provided a peroxyacid available oxygen (AvO) level of 3.5 ppm.

The results obtained for this bleaching performance test are shown below.

| Treatment and Average Relative Grade | | |
|---|---|---|
| | Detergent Granule Alone | Detergent Granule + 3.5 ppm AvO From Magnesium Bis (N—Decanoyl-6-Aminoperoxycaproate) |
| Naturally Soiled Fabrics | | |
| T-shirts | 0 | 1.4 s |
| Dish towels | 0 | 0.9 s |
| Pillowcases | 0 | 1.1 s |
| Artificially Stained Fabrics | | |
| Clay | 0 | 0.5 s |
| Spaghetti sauce | 0 | 1.2 s |
| Barbecue sauce | 0 | 0.0 |
| Tea | 0 | 3.4 s |
| Grass | 0 | 3.1 s |
| Menstrual blood | 0 | −0.1 |
| Blueberries | 0 | 1.4 s | s = statistically significant difference (confidence level of 90%) relative to the detergent granule alone treatment

What is claimed is:

1. A compound which has the formula:

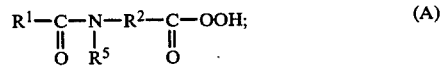
(A)

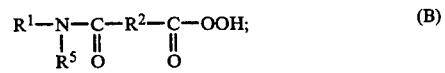
(B)

-continued

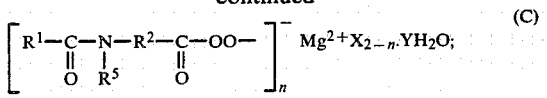

or

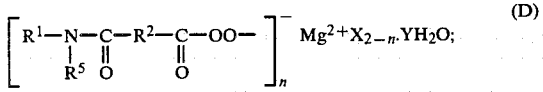

wherein R¹ is an alkyl, aryl or alkaryl group containing from about 1 to about 14 carbon atoms, R² is an alkylene, arylene or alkarylene group containing from about 1 to about 14 carbon atoms, R⁵ is H or an alkyl, aryl or alkaryl group containing from about 1 to about 10 carbon atoms, X is a compatible anion, n is 1 or 2, and Y is from 0 to about 6.

2. A compound according to claim 1 wherein the compound has the formula:

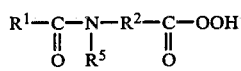

or

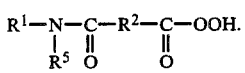

3. A compound according to claim 1 wherein R¹ is an alkyl group containing from about 6 to about 12 carbon atoms, R² is an alkylene group containing about 4 to about 8 carbon atoms, and R⁵ is H or methyl.

4. A compound according to claim 1 which has the formula:

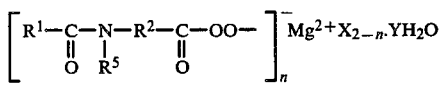

or

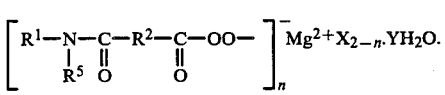

5. A compound according to claim 4 wherein R¹ is an alkyl group containing from about 6 to about 12 carbon atoms, R² contains from about 4 to about 8 carbon atoms, and R⁵ is H or methyl.

6. A bleach activator of the general formulas:

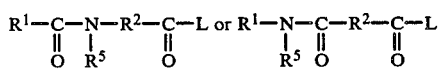

wherein R¹ is an alkyl, aryl or alkaryl group containing from about 1 to about 14 carbon atoms, R² is an alkylene, arlene or alkarylene group containing from about 1 to about 14 carbon atoms, and R⁵ is H or an alkyl, aryl or alkaryl group containing from about 1 to about 10 carbon atoms, and L is a leaving group, the conjugate acid of which has a pKa in the range of from about 4 to about 13.

7. A compound according to claim 6 wherein R¹ is an alkyl group containing from about 6 to about 12 carbon atoms, R² contains from about 4 to about 8 carbon atoms, and R⁵ is H or methyl.

8. The compound of claim 6 wherein L is a leaving group, the conjugate acid of which has a pK$_a$ in the range of from about 6 to about 11.

9. The compound of claim 6 wherein L is selected from the group consisting of:

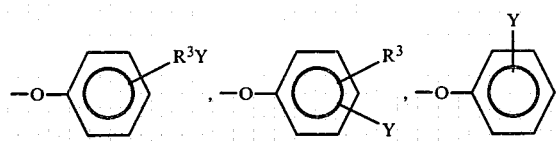

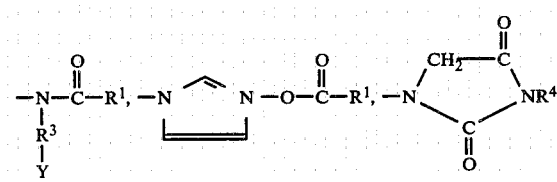

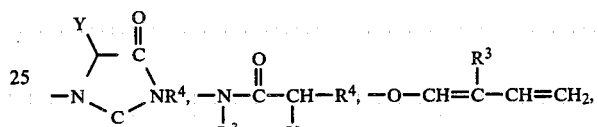

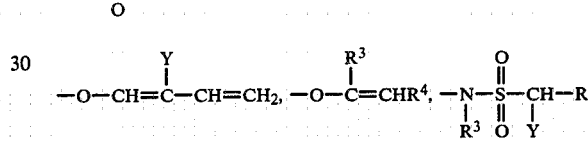

and mixtures thereof wherein R¹ is as defined in claim 1, R³ is an alkyl chain containing from about 1 to about 8 carbon atoms, R⁴ is H or R³, and Y is H or a solubilizing group.

10. The compound of claim 9 wherein Y is selected from the group consisting of: $-SO_3^-M^+$, $-COO^-M^+$, $-SO_4^-M^+$, $(-N^+R_4^3)X^-$ and $O\leftarrow NR_4^3$ and mixture thereof wherein R³ is an alkyl chain containing from about 1 to about 4 carbon atoms, M is a cation which provides solubility to the bleach activator and X is an anion which provides solubility to the bleach activator.

11. The compound of claim 10 wherein Y is selected from the group consisting of $-SO_3^-M^+$, $-COO^-M^+$ and mixtures thereof wherein M is selected from the group consisting of sodium, potassium and mixtures thereof.

12. The compound of claim 9 wherein L is selected from the group consisting of:

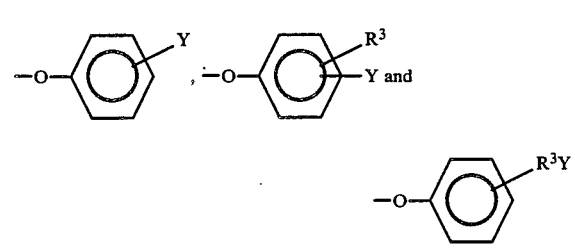

wherein R³ is an alkyl chain containing from about 1 to about 8 carbon atoms, Y is $-SO_3^-M^+$ or $-COO^-M^+$ wherein M is sodium or potassium.

13. The compound of claim 12 wherein L has the general formula:

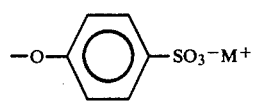

wherein M is sodium or potassium.

14. A bleaching composition comprising:
   (a) from about 1% to about 60% of a peroxygen bleaching compound capable of yielding hydrogen peroxide in an aqueous solution; and
   (b) from about 0.5% to about 40% of a bleach activator selected from

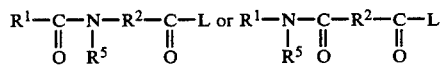

or mixtures thereof,
wherein $R^1$ is an alkyl, aryl or alkaryl group, and $R^2$ is an alkylene, arylene, or alkarylene group, each containing from about 1 to about 14 carbon atoms, $R^5$ is H or an alkyl, aryl or alkaryl group containing from about 1 to about 10 carbon atoms and L is a leaving group, the conjugate acid of which has a pKa in the range of from about 4 to about 13 wherein the molar ratio of hydrogen peroxide yielded by (a) to bleach activator (b) is greater than about 1.0.

15. A composition according to claim 14 also comprising from about 1% to about 30% of a detergent surfactant.

16. A composition according to claim 15 also comprising from about 10% to about 60% of a detergency builder.

17. The composition of claim 16 wherein the molar ratio of hydrogen peroxide yielded by (a) to bleach activator (b) is at least about 1.5.

18. The composition of claim 17 wherein the peroxygen bleaching compound is selected from the group consisting of sodium perborate, monohydrate, sodium perborate tetrahydrate, sodium carbonate peroxyhydrate, sodium pyrophosphate peroxyhydrate, urea peroxyhydrate, sodium peroxide and mixtures thereof.

19. The composition of claim 18 wherein the peroxygen bleaching compound is selected from the group consisting of sodium perborate monohydrate, sodium perborate tetrahydrate and mixtures thereof.

20. The composition of claim 14 wherein L is a leaving group, the conjugate acid of which has a pK$_a$ in the range of from about 6 to about 11.

21. The composition of claim 14 wherein L is selected from the group consisting of:

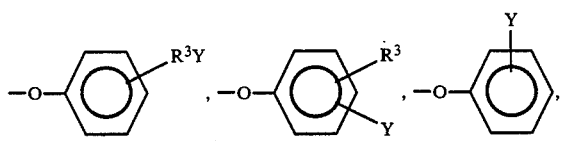

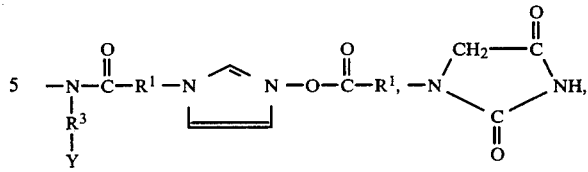

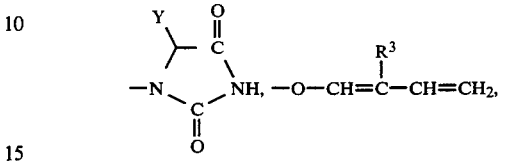

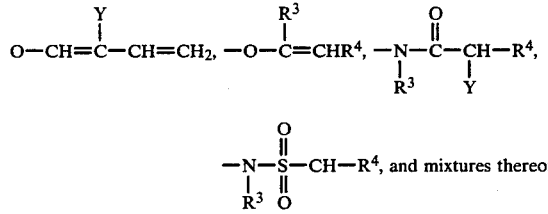

wherein $R^1$ is as defined in claim 1, $R^3$ is an alkyl chain containing from about 1 to about 8 carbon atoms, $R^4$ is H or $R^3$, and Y is H or a solubilizing group.

22. The composition of claim 21 wherein Y is selected from the group consisting of: $-SO_3^-M^+$, $-COO^-M^+$, $-SO_4^-M^+$, $(-N^+R_4^3)X^-$ and $O \leftarrow NR_4^3$ and mixtures thereof wherein $R^3$ is an alkyl chain containing from about 1 to about 4 carbon atoms, M is a cation which provides solubility to the bleach activator and X is an anion which provides solubility to the bleach activator.

23. The composition of claim 21 wherein Y is selected from the group consisting of $-SO_3^-M^+$, $-COO^-M^+$ and mixture thereof wherein M is selected from the group consisting of sodium, potassium and mixtures thereof.

24. The composition of claim 23 wherein L is selected from the group consisting of:

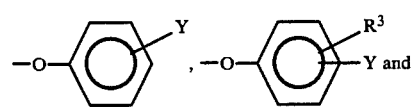

wherein $R^3$ is an alkyl chain containing from about 1 to about 8 carbon atoms, Y is $-SO_3^-M^+$ or $-COO^-M^+$ wherein M is sodium or potassium.

25. The composition of claim 24 wherein L has the general formula:

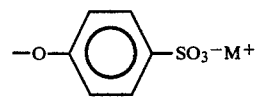

wherein M is sodium or potassium.

* * * * *